United States Patent
Takamatsu et al.

(10) Patent No.: US 6,552,235 B2
(45) Date of Patent: Apr. 22, 2003

(54) PROCESS FOR THE PREPARATION OF CYCLOHEXANOL

(75) Inventors: Yoshikazu Takamatsu, Kurashiki (JP); Tokitaka Kaneshima, Kurashiki (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/169,153

(22) PCT Filed: Dec. 26, 2000

(86) PCT No.: PCT/JP00/09250

§ 371 (c)(1),
(2), (4) Date: Jun. 28, 2002

(87) PCT Pub. No.: WO01/47845

PCT Pub. Date: Jul. 5, 2001

(65) Prior Publication Data

US 2003/0018223 A1 Jan. 23, 2003

(30) Foreign Application Priority Data

Dec. 28, 1999 (JP) ............................................. 11-372167

(51) Int. Cl.⁷ .......................... C07C 29/20; C07C 35/08

(52) U.S. Cl. ........................................ 568/835; 568/832

(58) Field of Search ................................. 568/835, 832, 568/822, 829, 831, 836, 895

(56) References Cited

FOREIGN PATENT DOCUMENTS

| JP | 60-115542 A | 6/1985 |
|---|---|---|
| JP | 7-247232 A | 9/1995 |
| JP | 9-249601 A | 9/1997 |

*Primary Examiner*—Johann Richter
*Assistant Examiner*—Elvis O. Price
(74) *Attorney, Agent, or Firm*—Birch, Stewart, Kolasch & Birch, LLP

(57) ABSTRACT

A method for producing cyclohexanol by subjecting cyclohexene to a hydration reaction in the presence of water using a solid acid as a catalyst in which as a reaction solvent, there is used an organic solvent having a solubility in water at 25° C. of not higher than 5% by weight, a boiling point which is at least 20° C. higher than that of the cyclohexanol produced, a conversion rate of not more than 3% under the hydration reaction conditions, and a solvent effect index of not less than 1.5 which indicates the effect of making the distribution of cyclohexene into the aqueous phase predominate.

5 Claims, No Drawings

PROCESS FOR THE PREPARATION OF CYCLOHEXANOL

This application is the national phase under 35 U.S.C. §371 of PCT International Application No. PCT/JP00/09250 which has an International filing date of Dec. 26, 2000, which designated the United States of America.

TECHNICAL FIELD

The present invention relates to a method for producing cyclohexanol, and, more particularly, to an industrially useful improvement of the method for producing cyclohexanol by hydrating cyclohexene using a solid acid as a catalyst.

PRIOR ART

As methods for producing cycloalkanols by hydrating cycloolefins such as cyclohexene, methods which use solid acid catalysts such as strongly acidic ion exchange resins and zeolites as catalysts have been well known. A feature of these methods is that removal of the catalysts is easier as compared with removal of homogeneous system catalysts such as mineral acids, but these methods suffer from the problem of low yield. In order to improve the yield, it has been proposed to add various organic solvents or organic additives.

For example, JP-A-58-194828 proposes to add organic solvents such as alcohols of 1–10 carbon atoms, halogenated hydrocarbons, ethers, acetone and methyl ethyl ketone. JP-A-62-120333 and JP-A-62-126141 propose addition of phenols, JP-A-64-13044 proposes addition of fluoroalcohols, JP-A-1-254634, JP-A-1-313447 and JP-A-4-247041 propose addition of aliphatic carboxylic acids, and JP-A-5-255162 proposes addition of benzoic acids. Moreover, JP-A-8-176041 proposes addition of benzoic acids having a substituent selected from the group consisting of alkoxy groups, aryloxy groups, alkylcarbonyl groups, arylcarbonyl groups, alkyloxycarbonyl groups, aryloxycarbonyl groups, aryl groups and arylalkyl groups. JP-A-9-263558 proposes addition of aromatic heterocyclic carboxylic acids. JP-A-7-247232 reports an effect exhibited by the coexistence with cycloalkanones, specifically, cyclohexanone. Furthermore, JP-A-9-249601 discloses a method in which a material having an action to enhance the distribution ratio of cycloalkenes into water is added alone or is allowed to coexist together with a material having an action to enhance the distribution ratio of cycloalkanols to organic layers, and it proposes addition of an alkylsulfonic acid or a heteropoly-acid in the former case and addition of an aromatic carboxylic acid, a phenol or a cyclic saturated carboxylic acid in the latter case. Moreover, in "Journal of Japan Chemical Society", 1989, (3), p.521–527, it is reported that the reaction rate and equilibrium conversion rate increase due to the presence of phenol, benzyl alcohol and methyl ethyl ketone.

However, these methods of adding various organic additives still have various problems in industrial working, and none of these methods can solve all of the problems. In many cases, there are problems that the yield is still insufficient even when the organic additives are used, and the use of solvents (organic additives) in large amounts is necessary for the improvement of the yield. Further problems are that the organic additives react with the starting material cyclohexene or the product cyclohexanol in the hydration reaction system, and the organic additives per se are not stable under the hydration reaction conditions, whereby by-products resulting from the organic additives are produced so as to cause loss of the organic additives and reduction in purity of the product cyclohexanol.

For example, use of the benzoic acid proposed in JP-A-5-255162, etc. has the problem that an esterification reaction takes place with the product cyclohexanol. Another problem is that purification of the reaction mixture by distillation is difficult to perform owing to the sublimation of benzoic acid.

In the case of using acetic acid proposed in JP-A-1-313447, since cyclohexyl acetate is produced in a large amount, a method for recovering each of cyclohexene, cyclohexanol and acetic acid is separately needed, which is disadvantageous for industrial working.

Although the phenols proposed in JP-A-62-120333, JP-A-62-126141, etc. are effective as solvents for improving the yield of cyclohexanol, since the cyclohexanol produced and the phenol form an azeotropic composition (maximum azeotropic point), there is a problem that distillation separation of cyclohexanol and phenol is impossible in industrial working, and, furthermore, there is a problem that since the solubility of phenol in water is high, namely, 8.5%, a loss of solvent increases in industrial working as mentioned hereinafter.

Benzyl alcohol disclosed in "Journal of Japan Chemical Society", 1989, (3), p.521–527 as a material having the effects of improving reaction rate and equilibrium conversion rate readily causes a hydration reaction under the hydration reaction conditions and is converted to dibenzyl ether, and, thus, the loss of solvent is great in industrial working. In addition, the above solvent effects cannot be obtained by dibenzyl ether and the effect of improving the conversion rate cannot be obtained.

Since cyclohexanone proposed in JP-A-7-247232 is somewhat lower in boiling point than the cyclohexanol to be produced, there will be a problem in distillation separation from cyclohexanol in industrial working. Furthermore, since cyclohexanone is also high in solubility in water, namely, 8.7%, there is a problem of an increase in loss of solvent in industrial practice.

On the other hand, new proposals have been made against these problems. For example, JP-A-9-286745 proposes to use a benzoic acid having a substituent on at least the 2-position as the organic additive to control esterification of the benzoic acid and the starting material cyclohexene. However, according to the examples in this patent publication, even when 2,6-dimethylbenzoic acid is used, complete inhibition of esterification thereof was not realized, and, further, the yield of cyclohexanol was only 14.7% by a batch reaction of 120° C.×1 hour using the additive in an amount of as large as 23 parts by weight. Thus, it cannot be said that a sufficient yield can be obtained.

JP-A-9-286746 proposes a method of using as an additive a cyclohexanecarboxylic acid having at least one substituent on the 1-, 2- or 6-position. According to the examples given therein, it is reported that the esterification can be inhibited by using 2-isopropylcyclohexanecarboxylic acid, but the yield of cyclohexanol is also only 13.6% by a batch reaction of 120° C.×1 hour using the additive in an amount of as large as 23 parts by weight. Thus, it cannot be said that a sufficient yield is obtained. Moreover, the organic additives used in these methods are extremely special ones.

On the other hand, for inhibiting deterioration of activity and for not deteriorating the performance of separation from the catalyst, JP-A-9-227429 and JP-A-9-227430 propose a method of feeding a solid organic additive in the molten state or as a solution to a reactor and a method of first contacting an aqueous slurry containing a solid acid catalyst with an organic additive in the presence of a cycloolefin. That is, in other words, it is suggested that the presence of the solid organic additive used in these methods has adverse effects of causing deterioration in catalyst activity with lapse of time and deterioration in separability of the catalyst in ordinary usage.

As mentioned above, the prior technologies as to the method of improving the yield of cyclohexanol by the addition of organic additives or solvents involve any one of the following problems in industrial practice.

1. The yield is still insufficient even when organic additive is used. Alternatively, a large amount of organic additive is necessary for improving the yield.

2. Impurities resulting from organic additive are produced in the hydration reaction system and the organic additive is lost with lapse of time, and, furthermore, the organic additive reacts with the starting material cyclohexene or the product cyclohexanol.

3. It is difficult to perform distillation separation between the organic additive per se or by-products resulting from the organic additive and the product cyclohexanol.

4. Deterioration of the activity of the hydration reaction catalyst is accelerated by the organic additive per se or by-products resulting from the organic additive.

5. The organic additive per se or by-products resulting from the organic additive adversely affect the separability between the catalyst and the reaction solution.

6. When the solvent (organic additive) is distributed into both phases of the cyclohexene phase and the aqueous phase and is high in solubility in the aqueous phase, problems arise in industrial practice. This is because in case there is a need to regenerate the catalyst in industrial practice, and when the reaction type is a stirring tank type which uses a catalyst slurry suspended in the aqueous phase, the solvent is also extracted out of the system together with the catalyst slurry in regeneration of the catalyst, and loss of the solvent added is great.

DISCLOSURE OF INVENTION

In the production of cyclohexanol by subjecting cyclohexene to hydration reaction in the presence of water using a solid acid as a catalyst, the present invention provides a solvent (an organic solvent) which can markedly improve the yield of cyclohexanol and simultaneously can solve all of the above-mentioned problems. Namely, according to the present invention, the yield of cyclohexanol can be markedly improved, no adverse effects are exerted on the selectivity of cyclohexanol, the change of catalyst activity with time or the separation of catalyst, and the product cyclohexanol can be easily recovered by distillation separation with only a small loss of solvent. Therefore, the object of the present invention is to provide a method for stably obtaining cyclohexanol of high purity in a very high yield.

As a result of intensive research conducted by the inventors in an attempt to solve the above problems, it has been found that in the production of cyclohexanol by subjecting cyclohexene to hydration reaction in the presence of water using a solid acid as a catalyst, the yield of cyclohexanol can be markedly improved, no adverse effects are exerted on the selectivity of cyclohexanol, the change of catalyst activity with time or the separation of catalyst, and the product cyclohexanol can be easily recovered by distillation separation with only a small loss of solvent, namely, cyclohexanol of high purity can be obtained stably and in a very high yield by using as a reaction solvent an organic solvent which is not higher than 5% by weight in solubility in water at 25° C., has a boiling point which is at least 20° C. higher than that of the cyclohexanol produced, is not more than 3% in conversion rate under the hydration reaction conditions, and is not less than 1.5 in solvent effect index which indicates the effect of making the distribution of cyclohexene into the aqueous phase predominate. Thus, the present invention has been accomplished.

That is, the present invention is a method for producing cyclohexanol by subjecting cyclohexene to a hydration reaction in the presence of water using a solid acid as a catalyst where an organic solvent which is not higher than 5% by weight in solubility in water at 25° C., has a boiling point which is at least 20° C. higher than that of the cyclohexanol produced, is not more than 3% in conversion rate under the hydration reaction conditions, and is not less than 1.5 in solvent effect index (which indicates the effect of making predominate the distribution of cyclohexene into the aqueous phase) is used as a reaction solvent. Preferably the solid acid is a zeolite, more preferably the zeolite is ZSM-5, and, furthermore, preferably the organic solvent used is isophorone or ethylene glycol monophenyl ether.

BEST MODE FOR CARRYING OUT THE INVENTION

The present invention will be specifically explained below.

The solid acid used as a catalyst in the present invention is an acidic solid substance, and there may be used zeolites, acidic ion exchange resins, heterocyclic poly-acids, and acidic oxides substantially insoluble in water, such as zirconium dioxide, tin dioxide and titanium dioxide. Among them, zeolites are preferred. Zeolite is a general term for crystalline aliminosilicates. As zeolite-analogous substances, there are reported crystalline metallosilicates which are zeolites in which a part of Si or Al is substituted with B, Fe, Cr, Ti, Ge, Ga or the like, and these crystalline metallosilicates are also included in the zeolites of the present invention.

Examples of zeolites used in the present invention are A-type zeolites, X,Y-type faujasite, L-type zeolites, mordenite, offretite, erionite, ferrierite, zeolite β, ZSM-4, ZSM-5, ZSM-8, ZSM-11, ZSM-12, ZSM-35, ZSM-48, etc. Preferred are zeolites having a pentasil structure, and especially preferred are ZSM-5 zeolites.

The zeolites used as catalysts in the present invention must be made into the acid type by ion exchange. The cation species introduced by ion exchange are not particularly limited as long as they can develop acidity, and mention may be made of, for example, protons, alkaline earth metals, metals of the titanium group, metals of the iron group, metals of the platinum group, rare earth metals, and the like. Among them, protons are preferred.

The organic solvents used as the reaction solvents in the method of the present invention have the following features. That is, the solubility in water at 25° C. is not higher than 5% by weight, the boiling point is at least 20° C. higher than that of the cyclohexanol produced, the conversion rate of the solvent under the hydration reaction conditions is not more than 3%, and the solvent effect index which indicates the effect of making the distribution of cyclohexene into the aqueous phase predominate is not less than 1.5.

The organic solvents used as the reaction solvents in the method of the present invention have a solubility in water at 25° C. of lower than 5% because this is advantageous in industrial practice of the reaction. That is, when the reaction is industrially carried out by a stirring tank type method which uses a catalyst slurry suspended in an aqueous phase as disclosed in JP-B-2-31056 and JP-A-9-227430 together with a schematic view of a continuous flowing reaction apparatus, it is necessary to recover from the reactor a part of the catalyst slurry deteriorated in activity due to the use for a long period of time and to regenerate the catalyst. In this case, the solvent dissolved in the aqueous phase is also extracted to result in loss of the solvent dissolved in the aqueous phase. In case of an organic solvent high in solubility in water, it is necessary to recover the aqueous phase and the organic solvent dissolved in the aqueous phase from the catalyst slurry, for example, by filtration or the like, which is considerably disadvantageous.

Therefore, the solubility in water at 25° C. of the organic solvent used as a reaction solvent in this reaction is preferably as low as possible, but the solubility correlates with the effect to make predominate the distribution of cyclohexene into the aqueous phase explained hereinafter, and, hence, the solubility in water at 25° C. of the organic solvent is preferably not higher than 3% by weight, more preferably not higher than 1.5% by weight.

The organic solvent used as a reaction solvent in the method of the present invention is an organic solvent having a normal boiling point which is at least 20° C. higher than that of cyclohexanol, namely, an organic solvent having a boiling point of not lower than 181° C. Furthermore, it is preferred that distillation separation from the product cyclohexanol is possible. Here, "distillation separation is possible" means that the organic solvent used does not produce an azeotropic composition with cyclohexanol. These factors are advantageous because the distillation separation between the product and the reaction solvent can be simply performed by known methods. On the other hand, it is known that the phenol which is a reaction solvent showing a high solvent effect and disclosed in JP-A-62-120333 and JP-A-62-126141 produces an azeotropic composition with cyclohexanol and it is impossible to separate by distillation. Thus, this is industrially very disadvantageous.

The organic solvent used as a reaction solvent in the method of the present invention is preferably an organic solvent having a boiling point within the range of 181–230° C. or 240° C. or higher, and more preferably an organic solvent having a boiling point within the range of 185–220° C., considering the separation from dicyclohexyl ether and cyclohexylcyclohexene which are high boiling point by-products in the cyclohexene hydration reaction.

The organic solvent used as a reaction solvent in the method of the present invention has a conversion rate of not more than 3% under the hydration reaction conditions of cyclohexene. The conversion rate of the organic solvent in the present invention is a conversion rate in the reaction of the organic solvent per se or the organic solvent with cyclohexene or cyclohexanol per 1 hour of batch reaction at the reaction temperature at which the hydration reaction of cyclohexene is carried out. In industrial working of the present invention, the solvent used for the reaction is separated from the product cyclohexanol and circulated for reuse. Therefore, taking into consideration the loss of the solvent and the product or the necessity for reuse of the solvent, preferably an organic solvent of not more than 1% in conversion rate under the hydration reaction conditions, more preferably an organic solvent that is substantially inert under the hydration reaction conditions (namely, does not react with cyclohexene and cyclohexanol) is used.

The organic solvent used as a reaction solvent in the method of the present invention exhibits an effect to make predominate the distribution of cyclohexene into an aqueous phase. The present reaction is carried out at a three-phase system of oil (cyclohexene)-water-catalyst. Since the solid acid catalyst such as zeolite is present in the aqueous phase and the reaction takes place on the catalyst, liquid-liquid distribution of cyclohexene greatly affects the reaction rate and the equilibrium conversion rate. As for the effect to make predominate the distribution of cyclohexene into the aqueous phase, "Journal of Japan Chemical Society", 1989, (3), p.521–527 mentions the results of measurement of the liquid-liquid distribution coefficient of cyclohexene in a solvent-free system and a phenol-containing system at 120° C. According to the results, the cyclohexene distribution coefficient into both phases of oil and water (cyclohexene concentration in the oil phase (mol %)/cyclohexene concentration in the aqueous phase (mol %)) is 3818 in the solvent-free system while it is 680 in the phenol-containing system. That is, it can be seen that the distribution of cyclohexene into the aqueous phase becomes predominate due to the presence of phenol. In the specification of JP-A-9-249601, phenol is defined to be a substance enhancing the distribution rate of cyclohexanol into an organic phase, but according to the disclosure of "Journal of Japan Chemical Society", 1989, (3), p.521–527 and the results of a tracing test conducted by the inventors, it is considered that the effect of phenol to improve the yield is obtained by the effect of making predominate the distribution of cyclohexene into the aqueous phase.

The organic solvent used in the present invention has a solvent effect index (defined below) of not less than 1.5. The solvent effect index in the present invention is defined to be a ratio of a distribution coefficient of cyclohexene in the absence of solvent at 120° C. and a distribution coefficient of cyclohexene in a solvent-containing system at 120° C. (distribution coefficient of cyclohexene in the absence of solvent/distribution coefficient of cyclohexene in a solvent-containing system), and it indicates an effect to make predominate the distribution of cyclohexene into an aqueous solution due to the presence of the organic solvent.

Detailedly, the solvent effect index in the present invention is obtained in the following manner. Cyclohexene/cyclohexanol/organic solvent/water are charged at a weight ratio of 56.7/13.3/30/100, and the distribution coefficient of cyclohexene (molar fraction of cyclohexene in oil phase/molar fraction of cyclohexene in aqueous phase) is obtained from the liquid composition of both phases of the oil phase and the aqueous phase in an equilibrium state kept at 120° C. The ratio of the resulting distribution coefficient of cyclohexene and the distribution coefficient of cyclohexene in a solvent-free system (measured at 120° C. by charging cyclohexene/cyclohexanol/water at a weight ratio of 56.7/13.3/100), namely, the ratio of distribution coefficient in solvent-free system/distribution coefficient in solvent-containing system, is the solvent effect index in the present invention.

The organic solvent used in the present invention has a solvent effect index of not less than 1.5, preferably not less than 2. It is generally considered that the larger the solvent effect index, the greater the effect to make predominate the distribution of cyclohexene into the aqueous solution. However, the solvent effect index correlates with the solubility of the organic solvent in the aqueous phase, and the organic solvent is selected, considering the balance with the solubility in water as aforementioned.

Here, the distribution coefficient of cyclohexene is measured by the following method. That is, an oil and water at the above weight ratio are charged in a pressure container under a nitrogen pressure, and sufficiently stirred and mixed at a rising temperature of 120° C., followed by reducing the stirring speed and leaving at rest for a time long enough to reach an equilibrium state. Thereafter, each of the oil phase and the aqueous phase is sampled in a solvent such as 1,4-dioxane, and the compositions of both the oil phase and the aqueous phase are obtained from analysis by gas chromatography and a Karl Fischer moisture meter. Thus, the distribution coefficient of cyclohexene is measured.

As examples of the organic solvents used in the present invention which have the above enumerated characteristics, mention may be made of phenethyl alcohol, ethylene glycol monophenyl ether (2-phenoxy ethanol), α-isophorone (3,5,5-trimethyl-2-cyclohexen-1-one), β-isophorone (3,5,5-trimethyl-3-cyclohexen-1-one), 2,4,4-trimethyl-2-cyclohexen-1-one, 3,3,5-trimethylcyclohexanone, 2,4,4-trimethylcyclohexanone, 2,6,6-trimethylcyclohexanone, 3,3,5,5-tetramethylcyclohexanone, etc. Preferred are ethylene glycol monophenyl ether and isophorones (which may be a mixture of α-isophorone and β-isophorone because they show similar solvent effects), and more preferred are isophorones. These organic solvents may be used each alone or in admixture of a plurality of them.

The characteristics of organic solvents used as reaction solvents in the present invention will be explained, taking as an example isophorone which is a preferable organic solvent.

The solubility in water at 25° C. of isophorone which is a preferable organic solvent in the method of the present invention is 1.2 g/100 ml (see HAZARDOUS SUBSTANCES DATA BANK, ISOPHORONE, 920123). Isophorone produces a minimum azeotropic composition with water. Therefore, when the present reaction is industrially practiced by the stirring tank type method using a catalyst slurry suspended in an aqueous phase as shown above, use of isophorone is advantageous in that the amount of isophorone in the catalyst slurry extracted out of the system at the step of regeneration of catalyst is small, and, furthermore, it is also very advantageous in that isophorone in the catalyst slurry can be simply recovered by distillation utilizing the azeotropy with water and thus loss of the solvent can be considerably reduced.

As for the boiling point of isophorone, the boiling point of α-isophorone is 215° C. and that of β-isophorone is 186° C., and there is a difference of 25–50° C. in the boiling point of isophorone and that of cyclohexanol, and, furthermore, since no azeotropic composition is produced, isophorone can be separated and recovered by the generally employed simple distillation separation methods.

Isophorone causes no hydration reaction under the reaction conditions of the present invention, and, further, has no reactivity with the starting material cyclohexene and the product cyclohexanol and is present very stably. Furthermore, due to its molecular structure, isophorone is hindered from diffusion into the pores of ZSM-5 zeolite suitably used in the present invention, and hence adverse effects on the catalyst activity can be avoided, selectivity for shape is also not affected, and, rather, the contribution of surface active points is inhibited resulting in an improvement in the selectivity of cyclohexanol. For this reason, isophorone is advantageous for industrial working.

The solvent effect index of isophorone obtained by carrying out the liquid-liquid equilibrium measurement shown above is 2.19, and it can be seen that isophorone is an organic solvent which makes predominate the distribution of cyclohexene into an aqueous phase.

As explained above, isophorone which is suitable as a reaction solvent in the method of the present invention develops the effect to make predominate the distribution of cyclohexene into the aqueous phase in spite of its low solubility in water, and, further, isophorone has the surprising effects that it can be easily separated from cyclohexanol by distillation and, furthermore, it has no adverse influence on the selectivity of cyclohexanol and change of catalyst activity with time. Thus, it can be said that isophorone is an excellent solvent which solves the problems in conventional methods for the production of cyclohexanol.

Isophorone is obtained by trimerization of acetone, and is used as industrial products comprising α-isophorone containing a slight amount of β-isophorone (isomer), mainly, as solvents for resins.

Isophorone is preferably of high purity, but industrial products may be used as they are. General purity of isophorone of industrial products is usually about 97–99.8% including β-isophorone as an isomer.

The amount of water used in the method of the present invention is suitably 1–100 moles based on 1 mole of cyclohexene, and the amount of the catalyst used is suitably 0.01–100 in weight ratio based on cyclohexene. The amount of the organic solvent as a reaction solvent is 0.05–10, preferably 0.1–5, more preferably 0.25–1 in weight ratio based on cyclohexene.

The reaction type in the method of the present invention may be any of batch type, continuous type, reaction distillation type, and the like, and the continuous type includes the fixed-bed flowing reaction type and the stirring tank flowing reaction type.

The reaction temperature in the method of the present invention is 50–200° C., preferably 80–160° C. If the reaction temperature is lower than 50° C., the reaction rate is slow, which is not practical, and if the reaction temperature exceeds 200° C., equilibrium of the reaction is one-sided, which is disadvantageous.

The reaction pressure in the method of the resent invention is not particularly limited as long as a liquid phase is maintained at the reaction temperature, and is preferably 0.1–5 MPa. The reaction atmosphere is preferably an inert gas atmosphere such as nitrogen, helium, argon, carbon dioxide or the like, and preferably the oxygen content is low.

The present invention will be explained by the following examples. These examples should not be construed as limiting the invention in any manner, and changes and modifications may be made without departing from the spirit of the invention.

EXAMPLE 1

Synthesis of ZSM-5 Zeolite-A

ZSM-5 zeolite was synthesized by the method disclosed in Example 1 of Japanese Patent No. 2844098.
(1) Synthesis of Seed Slurry A solution prepared by dissolving 0.61 Kg of $Al_2(SO_4)_3 \cdot 16H_2O$ and 0.1 Kg of 1,3-dimethylurea in 15 Kg of water was added to a solution obtained by adding 0.05 Kg of NaOH and 4.0 Kg of water to 8.0 Kg of an aqueous sodium silicate solution manufactured by Fuji Chemical Co., Ltd. ($SiO_2$: 26% by weight, $Na_2O$: 7.0% by weight) while stirring, and 10 Kg of sulfuric acid of 5% by weight was added thereto to obtain a homogeneous gel. This gel was charged in an autoclave of 50 liters in internal volume and crystallized at 160° C. for 10 hours while stirring at a stirring power of 0.5–1 $KW/m^3$. The resulting slurry was cooled to obtain a seed slurry.

(2) Final Synthesis (Synthesis of ZSM-5 Zeolite-A)

To 12.6 Kg of the seed slurry were added 5.3 Kg of the aqueous sodium silicate solution used in the above (1), 30 g of NaOH and 2.67 Kg of water. Furthermore, while stirring, thereto was added a solution prepared by dissolving 0.41 Kg of $Al_2(SO_4)_3 \cdot 16H_2O$ and 0.06 Kg of 1,3-dimethylurea in 10 Kg of water, and 6.67 Kg of sulfuric acid of 5% by weight was added to obtain a homogeneous gel. This gel was charged in an autoclave of 50 liters and crystallized at 150° C. for 30 hours while stirring at a stirring power of 0.5–1 $KW/m^3$. The resulting slurry was cooled, recovered and filtered by a centrifugal extractor. Then, the filtration was repeated while washing with water. The resulting filter cake was dried at 120° C. for 8 hours to obtain a powdery zeolite-A. The resulting zeolite-A was analyzed by an X-ray diffraction apparatus (Model RAD-3A manufactured by Rigaku Co., Ltd.) to find that the diffraction pattern was of ZSM-5 and the zeolite-A was ZSM-5 zeolite. The resulting ZSM-5 zeolite-A was fired at 500° C. for 6 hours while flowing air, and then 1 Kg of the fired ZSM-5 zeolite-A was added to 10 liters of 1N aqueous nitric acid solution, followed by ion exchanging at 60° C. for 4 hours, filtration, washing with water, and drying at 120° C. for 12 hours to obtain H-ZSM-5 zeolite-A. The resulting H-ZSM-5 zeolite-A was subjected to elemental analysis by an electron probe micro-analyzer (Model X-650 manufactured by Hitachi Ltd.; X-ray detector: an energy dispersion type X-ray analyzer Model EMAX-5770W manufactured by Horiba Mfg. Co., Ltd.) to find that the molar ratio of silica/alumina ($SiO_2/Al_2O_3$) was 29. As to the particle diameter, it was found from a scanning type electron photomicrograph that the zeolite was a platy particulate having a thickness of not more than 0.2 μm in the portion having the narrowest width.

Hydration Reaction of Cyclohexene 30 g of the resulting H-ZSM-5 zeolite-A catalyst and 81 g of water were charged in a glass autoclave A and heated to 120° C. with stirring under application of a nitrogen pressure of 0.5 MPa. Separately, 61 g of cyclohexene and 20 g of isophorone were charged in a glass autoclave B and heated to 120° C. under application of a nitrogen pressure of 0.6 MPa. Thereafter, the cyclohexene/isophorone mixed liquid was sent under pressure from the glass autoclave B to the glass autoclave A, and the reaction was started. After the reaction for 1 hour, the stirring was stopped, and the oil phase was sampled and analyzed by gas chromatography. At the sampling, the reaction mixture separated to two phases of oil phase and aqueous phase immediately after stopping of stirring. Yield and selectivity of cyclohexanol were as follows.

Yield of cyclohexanol: 24.3%; Selectivity: 99.7%

Main impurities were methylcyclopentene and dicyclohexyl ether which were by-products in the hydration reaction of cyclohexene. The isophorone showed no change.

From this Example and Comparative Example 1 where isophorone was not used, it can be seen that the yield of cyclohexanol (reaction rate, equilibrium conversion rate) can be remarkably improved by using isophorone as a solvent, and in this case, by-products which are impurities resulting from the solvent are not produced at all and the solvent is very stable, and the addition of isophorone does not adversely affect oil and water separation.

EXAMPLE 2

Synthesis of ZSM-5 Zeolite-B

ZSM-5 zeolite was synthesized by the method disclosed in Example 7 of Japanese Patent No. 2844098.

(1) Synthesis of Seed Slurry (1)

2.5 Kg of water was added to 5.35 Kg of an aqueous sodium silicate solution manufactured by Fuji Chemical Co., Ltd. ($SiO_2$: 26% by weight, $Na_2O$: 7.0% by weight) to obtain a uniform solution. This solution was charged in an autoclave of 50 liters in internal volume, and a solution prepared by dissolving 0.4 Kg of $Al_2(SO_4)_3 \cdot 16H_2O$ and 0.26 Kg of concentrated sulfuric acid in 15 Kg of water was fed by a pump to the autoclave at room temperature over a period of 30 minutes while stirring the content of the autoclave. Then, the content was crystallized under the conditions of 170° C., 30 hours and 250 rpm. The resulting slurry was cooled to obtain a seed slurry (1).

(2) Synthesis of Seed Slurry (2)

5.65 Kg of the aqueous sodium silicate solution used in the above (1), 28 g of NaOH and 45 g of $NaAlO_2$ were added to 2.21 Kg of water to obtain a uniform solution. This solution and 10.5 Kg of the seed slurry (1) were charged in an autoclave of 50 liters in internal volume, and a solution prepared by dissolving 0.424 Kg of $Al_2(SO_4)_3 \cdot 16H_2O$ and 50 g of $NaAlO_2$ in 10 Kg of water was fed by a pump to the autoclave at room temperature over a period of 30 minutes while stirring at 150 rpm. Furthermore, a solution prepared by dissolving 0.2 Kg of concentrated sulfuric acid in 5.84 Kg of water was fed by a pump to the autoclave over a period of 15 minutes followed by heating to 190° C. and crystallizing over 6 hours. The resulting slurry was cooled and recovered to obtain a seed slurry (2).

(3) Final Synthesis (Synthesis of ZSM-5 Zeolite-B)

5.65 Kg of the aqueous sodium silicate solution used in the above (1), 28 g of NaOH and 45 g of $NaAlO_2$ were added to 2.21 Kg of water to obtain a uniform solution. To this solution was added 10.5 Kg of the seed slurry (2) to prepare a homogeneous slurry. This slurry was charged in an autoclave of 50 liters, and while stirring at room temperature and at 150 rpm, thereto was fed by a pump a solution prepared by dissolving 0.424 Kg of $Al_2(SO_4)_3 \cdot 16H_2O$ and 50 g of $NaAlO_2$ in 10 Kg of water over a period of 30 minutes. Furthermore, an aqueous solution obtained by dissolving 0.2 Kg of concentrated sulfuric acid in 5.84 Kg of water was fed thereto by a pump over a period of 15 minutes, followed by heating to 165° C. and crystallizing over a period of 30 hours while stirring at 150 rpm. The resulting slurry was cooled, recovered and filtered by a centrifugal extractor. Then, the filtration was repeated while washing with water. The resulting filter cake was dried at 120° C. for 8 hours to obtain about 1.7 Kg of a powdery zeolite-B. The X-ray diffraction pattern of the resulting zelite-B was of ZSM-5 and the zeolite-B was ZSM-5 zeolite. Furthermore, as a result of the elemental analysis, the molar ratio of silica/alumina ($SiO_2/Al_2O_3$) of the ZSM-5 zeolite-B was 29. It was found that the zeolite was a very fine particulate having a particle diameter of about 0.05 μm. 1 Kg of the ZSM-5 zeolite-B was added to 10 liters of 1N aqueous nitric acid solution, followed by ion exchanging at room temperature for 4 hours, filtration, washing with water, and then drying at 120° C. for 12 hours to obtain H-ZSM-5 zeolite-B.

Hydration Reaction of Cyclohexene

The hydration reaction of cyclohexene was carried out in the same manner as in Example 1, except that the resulting H-ZSM-5 zeolite-B was used as the catalyst. The results of the reaction were as follows.

Yield of cyclohexanol: 24.9%; Selectivity: 99.5%

EXAMPLE 3

Synthesis of ZSM-5 Zeolite-C

ZSM-5 zeolite was synthesized by the method disclosed in Example 1 of Japanese Patent No. 2577941.

(1) Synthesis of Seed Slurry

2 Kg of water and 25 g of NaOH were added to 5.3 Kg of the Q brand aqueous sodium silicate solution manufactured by Fuji Chemical Co., Ltd. to obtain a uniform solution. This solution was charged in an autoclave of 50 liters in internal volume, and a solution prepared by dissolving 0.4 Kg of $Al_2(SO_4)_3 \cdot 18H_2O$ and 0.3 Kg of concentrated sulfuric acid in 15 Kg of water was fed by a pump to the autoclave at room temperature over a period of 60 minutes while stirring. Then, crystallization was carried out under the conditions of 180° C., 10 hours and 250 rpm. The resulting slurry was cooled to obtain a seed slurry.

(2) Final Synthesis (Synthesis of ZSM-5-C)

5.7 Kg of the Q brand aqueous sodium silicate solution manufactured by Fuji Chemical Co., Ltd. and 28 g of NaOH were added to 2.2 Kg of water to obtain a uniform solution. To this solution was added 10.5 Kg of the seed slurry obtained in the above (1) to prepare a homogeneous slurry. This slurry was charged in an autoclave of 50 liters, and while stirring at room temperature and at 250 rpm, thereto was fed by a pump over 60 minutes an aqueous solution prepared by dissolving 0.42 Kg of $Al_2(SO_4)_3 \cdot 18H_2O$ and 0.3 Kg of concentrated sulfuric acid in 16 Kg of water. Then, the slurry was heated to 150° C. and crystallized over a period of 30 hours while stirring at 250 rpm. The resulting slurry was cooled, recovered and filtered by a centrifugal extractor. Then, the filtration was repeated while washing with water in an amount of 8 times. The resulting filter cake was dried at 120° C. for 10 hours to obtain 1.7 Kg of a powdery zeolite. The X-ray diffraction pattern of the resulting zeolite-C was of ZSM-5 and thus the zeolite-C was ZSM-5 zeolite. The ZSM-5 zeolite-C had $SiO_2/Al_2O_3$ of 28, and as for the particle diameter, it was an agglomerate of primary particles of not more than 0.1 μm and was a particulate forming columnar secondary particles of about 0.5×0.5×1 μm. 100 g of the resulting ZSM-5 zeolite-C was added to 1 liter of 1N aqueous nitric acid solution, followed by ion exchanging for 4 hours at room temperature, filtration, washing with water, and then drying at 120° C. for 12 hours to obtain H-ZSM-5 zeolite-C.

Hydration Reaction of Cyclohexene

The hydration reaction of cyclohexene was carried out in the same manner as in Example 1, except that the resulting H-ZSM-5 zeolite-C was used as the catalyst. The results of the reaction were as follows.

Yield of cyclohexanol: 24.3%; Selectivity: 99.6%

EXAMPLE 4

Hydration Reaction of Cyclohexene

The hydration reaction of cyclohexene was carried out in the same manner as in Example 1, except that ethylene glycol monophenyl ether, phenethyl alcohol and 3,3,5-trimethylcyclohexanone were respectively used as the reaction solvents. The results of the reactions are shown in Table 1, and characteristics of the organic solvents used in this Example are shown in Table 2.

From this Example and Comparative Example 1 where solvent was not used, it can be seen that yield of cyclohexanol (reaction rate, equilibrium conversion rate) can also be remarkably improved by using the above organic solvents as reaction solvents.

EXAMPLE 5

Continuous Stirring Tank Flowing Reaction for Hydration of Cyclohexene

A continuous flowing reaction test of cyclohexene hydration reaction was conducted under the following conditions. The H-ZSM-5 zeolite-A used in Example 1 was used as the catalyst.

Reaction device: A stainless steel autoclave of 1 liter in internal volume.

Holdup amounts in the reaction vessel
 Oil: 240 ml
 Slurry: 240 ml

Slurry concentration: catalyst 30% by weight

Feed rate of oil (cyclohexene/isophorone): 170 ml/Hr

Weight ratio of cyclohexene/isophorone: 0.7/0.3

Reaction temperature: 120° C.

Reaction pressure: Pressurized to 0.7 MPa with nitrogen.

Oil was continuously extracted from an overflow nozzle under such stirring conditions as forming a phase comprising only the oil in the upper part of the reaction vessel, and water consumed for the reaction was optionally introduced by a pump. The reaction was continued for 120 hours. During the operation, no catalyst slurry flowed out, and it can be seen that even when isophorone solvent is used, the oil-water separation is not adversely affected. The results of the reaction are shown in Table 3.

From this Example and Comparative Example 5, the cyclohexene hydration flowing reaction using isophorone as a solvent is evaluated. That is, it is confirmed that the yield (productivity) of cyclohexanol is improved. Furthermore, it is recognized that no significant difference is seen in the tendency of deterioration of catalyst activity between the solvent-containing system and the solvent-free system, and isophorone does not affect the deterioration of catalyst activity.

EXAMPLE 6

Continuous Fixed-bed Flowing Reaction for Hydration of Cyclohexene

A continuous fixed-bed flowing reaction test of a cyclohexene hydration reaction was conducted under the following conditions using ethylene glycol monophenyl ether (EGMPE) as a reaction solvent. As a reaction apparatus, a stainless steel reaction vessel of 26.5 mm in internal diameter provided with a heating medium jacket was used. In the upper part of the reaction vessel, there were provided feed openings for water and oil, and in the lower part of the reaction vessel, oil and water in the mixed state were led to a reaction mixture storage tank through a pressure regulating valve, and oil and water were separated from each other in the reaction mixture storage tank. ZSM-5 zeolite (silica/alumina molar ratio=50) manufactured by Engelhard Co., Ltd. with addition of 20 wt % of an alumina binder was extrusion molded to a size of 1/16 inch in external diameter and 5 mm in length, and this was used as the catalyst. The height of the catalyst layer was 240 mm. The continuous reaction was carried out by an oil-water falling parallel flow sealing reaction method under the following conditions.

Filling amount of catalyst in reaction vessel: 87.2 g

Feed rate of oil: 24.5 g/Hr

Feed rate of water: 12.0 g/Hr

Oil composition (weight ratio of cyclohexene/EGMPE): 70/30

Reaction temperature: 135° C. (heating medium circulating temperature) 124–134° C. (temperature of catalyst medium layer)

Reaction pressure: Set at 2 MPa (liquid sealing reaction pressure)

The oil phase discharged into the reaction mixture storage tank was analyzed by gas chromatography to obtain the results of the reaction. At the time of starting of the reaction, only cyclohexene was fed, and after a lapse of 20 hours from the starting of the reaction, the starting material was changed to a mixed liquid of cyclohexene/ethylene glycol monophenyl ether=70/30 (weight ratio), and thereafter the reaction was continued for 150 hours. The results of the reaction are shown in Table 4.

From this Example, it can be seen that in the case of using ethylene glycol monophenyl ether as the reaction solvent, a high yield of cyclohexanol is also obtained, and the catalyst activity is not deteriorated. When the ethylene glycol monophenyl ether solvent was used, conversion to ethylene glycol cyclohexylphenyl ether was recognized under the hydration reaction conditions, but the conversion rate was less than 1% and was lowered greatly with the lapse of time. Thus, it is suggested that the side reaction took place at the surface active points of the zeolite. Moreover, since the by-product is higher in boiling point than the solvent, it can be recovered by distillation separation and separately restored to the ethylene glycol monophenyl ether.

EXAMPLE 7

Experiment on Recovery of Cyclohexanol by Distillation 503 g of the reaction product obtained by the continuous flowing reaction of Example 5 was subjected to batch-wise distillation separation under a reduced pressure of 10.67–12.66 kPa using a 15-plate Oldershaw type glass distillation column (plate efficiency: about 60%). In this case, the operation was conducted by optionally setting the reflux ratio depending on the degree of concentration. After recovery of 274 g as an initial boiling matter which comprised mostly cyclohexene, 82 g of cyclohexanol fraction was recovered under the conditions of about 12.6 kPa, a bottom temperature of about 140° C., and a top temperature of about 103–104° C. The cyclohexanol fraction was analyzed to find that recovery of cyclohexanol in the initial fraction and the final fraction was 99.2%, the content of isophorone in the cyclohexanol final fraction was less than the limit of detection, 50 ppm of methylcyclopentanols and 90 ppm of cyclohexanone were contained as impurities, and the purity of cyclohexanol was higher than 99.9%.

From this Example, it can be seen that the distillation separation between the product cyclohexanol and isophorone which is a suitable reaction solvent in the present invention can be simply performed by a general distillation separation method, and cyclohexanol obtained by the method of the present invention is of very high purity.

Comparative Example 1

The reaction was carried out in the same manner as in Example 1, except that isophorone was not added. At the time of sampling, separation into two phases of oil and water occurred immediately after stopping of the stirring. Yield of cyclohexanol after each reaction time was as follows.

Catalyst: H-ZSM-5 zeolite-A
1 Hour: yield of cyclohexanol: 12.6%
2 Hours: yield of cyclohexanol: 14.8%
3 Hours: yield of cyclohexanol: 15.8%

Comparative Example 2

The reaction was carried out in the same manner as in Example 2, except that isophorone was not added. Yield of cyclohexanol after each reaction time was as follows.

Catalyst: H-ZSM-5 zeolite-B
1 Hour: yield of cyclohexanol: 12.3%
2 Hours: yield of cyclohexanol: 14.6%
3 Hours: yield of cyclohexanol: 15.7%

Comparative Example 3

The reaction was carried out in the same manner as in Example 3, except that isophorone was not added. Yield of cyclohexanol after each reaction time was as follows.

Catalyst: H-ZSM-5 zeolite-C
1 Hour: yield of cyclohexanol: 12.5%
2 Hours: yield of cyclohexanol: 14.9%
3 Hours: yield of cyclohexanol: 15.3%

From Comparative Examples 1–3, it can be seen that when reaction solvents are not used, the yield of cyclohexanol remains at a low level due to equilibration even if a known catalyst having high activity is used.

Comparative Example 4

The reaction was carried out in the same manner as in Example 1, except that benzyl alcohol was used as the solvent. Yield of cyclohexanol after each reaction time was as follows.

Catalyst: H-ZSM-5 zeolite-A
1 Hour: yield of cyclohexanol: 17.2%
2 Hours: yield of cyclohexanol: 21.5%

In this Comparative Example, the conversion rate of the benzyl alcohol as the reaction solvent to dibenzyl ether as a dehydration condensation reaction product reached 11.4% after 1 hour and 16.0% after 2 hours, and, in addition, the production of several kinds of by-products such as phenethyl alcohol was recognized.

As can be seen from this Comparative Example, benzyl alcohol disclosed in "Journal of Japan Chemical Society", 1989, (3) P.521–527 has a solvent effect, but undergoes dehydration condensation under hydration reaction conditions and is converted to dibenzyl ether, which does not exhibit a solvent effect. Therefore, it must be said that such unstable solvent cannot be industrially used.

Comparative Example 5

The continuous flowing reaction test on the hydration reaction of cyclohexene was conducted in the same manner as in Example 5, except that only cyclohexene as a starting material was fed at a feeding rate of 170 ml/Hr. The results of the reaction are shown in Table 5.

Comparative Example 6

Behavior in Distillation Separation of Cyclohexanol/phenol

A mixture comprising 62.2 mol % of cyclohexanol and 37.8 mol % of phenol was charged in a flask of 500 ml and was subjected to distillation separation experiment using a batch-wise vacuum distillation apparatus equipped with a fractionating column. The distillation was continued until the temperature in the flask became constant after starting the distillation under a pressure of 7.33 kPa, and when the temperature was stabilized at about 116° C., the residual solution in the flask was sampled and the composition of the sample was analyzed by gas chromatography.

The composition in the residual solution comprised 19.1 mol % of cyclohexanol and 80.9 mol % of phenol, and the composition of the distillate in total comprised 81.8 mol % of cyclohexanol and 18.2 mol % of phenol.

Cyclohexanol 19 mol % (pressure: 7.33 kPa, temperature: 116° C.) of the maximum azeotropic composition of cyclohexanol/phenol obtained from the results of the distillation experiment nearly agreed with cyclohexanol 22 mol % (pressure: 7.33 kPa, temperature: 109° C.) of the azeotropic composition separately calculated by the vapor-liquid equilibrium computation method (UNIFAC).

From this Comparative Example, it can be seen that phenol reported to exhibit an excellent solvent effect in conventional technologies cannot be separated by distillation from the product cyclohexanol, and is seriously disadvantageous in industrial working.

TABLE 1

Results of batch-wise hydration reaction of cyclohexene using various solvents

| Kind of solvent | Yield NOL (mol %) | Solvent of convertion rate (%) |
|---|---|---|
| Comparative Example 1 (Solvent-free system) | 12.6 | — |
| Isophorone | 24.3 | 0.00 |
| Ethylene glycol monophenyl ether | 25.5 | 0.70 |
| Phenethyl alcohol | 21.1 | 0.35 |
| 3,3,5-Trimethylcyclohexanone | 21.8 | 0.00 |

| Initial introduction amount | |
|---|---|
| Catalyst H-ZSM-5-A | 30 g |
| Water | 81 g |
| Solvent | 20 g |
| Cyclohexene | 61 g |
| Cyclohexene (solvent-free system) | 81 g |
| Reaction temperature | 120° C. |
| Reaction time | 1 hour |

TABLE 3

Results of flowing reaction of hydration of cyclohexene using isophorone solvent

| Reaction time (Hr) | Cyclohexanol Yield (%) | Productivity (g-NOL/g-cat/Hr) | Relative activity (%) |
|---|---|---|---|
| 10 | 21.6 | 0.329 | 100.0 |
| 60 | 19.8 | 0.302 | 91.7 |
| 120 | 19.2 | 0.293 | 88.9 |

| | |
|---|---|
| Feed rate | 170 ml/Hr |
| Cyclohexene | 100.0 g/Hr |
| Isophorone | 42.9 g/Hr |
| Isophorone concentration | 30.0 wt % |
| Catalyst amount H-ZSM-5-A | 80.0 g |
| Slurry concentration | 30.0 wt % |

Relative activity: Calculated assuming the yield after 10 hours to be 100.

TABLE 4

Results of fixed-bed flowing reaction of hydration of cyclohexene using ethylene glycol monophenyl ether solvent

| Reaction time (Hr) | Cyclohexanol Yield (%) | Productivity (g-NOL/g-cat/Hr) | Relative activity (%) | Solvent conversion rate (%) |
|---|---|---|---|---|
| 10 | 9.4 | 0.023 | 100.0 | |
| 20 | 9.2 | 0.022 | 97.9 | |
| 25 | 18.0 | 0.043 | 100.0 | 0.84 |

TABLE 2

Characteristics and properties of various organic solvents used in Example 4

| Kind of solvent | | No | IPN | EGMPE | PhEtOH | TMCHNON |
|---|---|---|---|---|---|---|
| Organic solvent Boiling point (° C.) | | | 215 | 245 | 219 | 190 |
| Solubility in water (25° C.) (g/100 ml) | | | 1.20 | 2.70 | 2.00 | 0.80 |
| Oil phase mol % | Water | 7.376 | 10.888 | 16.236 | 12.642 | 7.807 |
| | HE | 78.988 | 59.909 | 57.041 | 57.869 | 61.945 |
| | NOL | 13.636 | 10.850 | 10.301 | 10.548 | 11.126 |
| | SLV | | 18.354 | 16.422 | 18.942 | 19.122 |
| Aqueous phase mol % | Water | 99.729 | 99.699 | 99.459 | 99.460 | 99.777 |
| | HE | 0.019 | 0.032 | 0.034 | 0.031 | 0.032 |
| | NOL | 0.252 | 0.160 | 0.157 | 0.146 | 0.166 |
| | SLV | | 0.110 | 0.350 | 0.363 | 0.025 |
| Distribution coefficient of cyclohexene | | 4131 | 1884 | 1681 | 1846 | 1929 |
| Solvent effect index | | 1.00 | 2.19 | 2.46 | 2.24 | 2.14 |

IPN Isophorone
PhEtOH Phenethyl alcohol
TMCNON 3,3,5-Trimethylcyclohexanone
HE Cyclohexene
NOL Cyclohexanol
SLV Organic solvent added

TABLE 4-continued

Results of fixed-bed flowing reaction of
hydration of cyclohexene using ethylene glycol
monophenyl ether solvent

| 80 | 17.3 | 0.041 | 96.1 | 0.63 |
|---|---|---|---|---|
| 150 | 16.8 | 0.040 | 93.3 | 0.42 |

*:Only cyclohexene was fed for 20 hours after starting of the reaction. Thereafter, cyclohexene/ethylene glycol monophenyl ether = 70/30 (weight ratio) were fed.

Feed rate

| Oil | 24.5 g/Hr |
|---|---|
| Water | 12.0 g/Hr |
| Solvent concentration | 30.0 wt % |
| Catalyst | Extrusion molded product of H-ZSM-5 manufactured by Engelhard Co., Ltd. |
| Binder concentration | 20.0 wt % |
| Filling amount of catalyst | 87.2 g |
| ZSM-5 | 69.8 g |
| Heating medium circulating temperature | 135° C. |
| Catalyst layer temperature | 124–134° C. |
| Reaction pressure | 2 MPa |

Relative activity: After addition of the solvent, this was calculated assuming the yield after 25 hours to be 100.

TABLE 5

Results of flowing reaction of hydration of cyclohexene in solvent-free system

| Reaction time (Hr) | Cyclohexanol Yield (%) | Productivity (g-NOL/g-cat/Hr) | Relative activity (%) |
|---|---|---|---|
| 10 | 10.7 | 0.226 | 100.0 |
| 60 | 9.5 | 0.200 | 88.8 |
| 120 | 9.2 | 0.193 | 85.7 |

| Feed rate | 170 ml/Hr |
|---|---|
| Cyclohexene | 137.9 g/Hr |
| Isophorone | 0.0 g/Hr |
| Isophorone concentration | 0.0 wt % |
| Catalyst amount H-ZSM-5-A | 80.0 g |
| Slurry concentration | 30.0 wt % |

Relative activity: Calculated assuming the yield after 10 to be 100.

INDUSTRIAL APPLICABILITY

According to the present invention, the yield of cyclohexanol is markedly improved, change in catalyst activity and separation of catalyst are not adversely affected, and, furthermore, recovery of the product cyclohexanol by distillation separation can be easily performed, and the loss of solvent used is small. That is, cyclohexanol of high purity can be stably obtained in a high yield. Therefore, the present invention is very advantageous for the industrial production of cyclohexanol.

What is claimed is:

1. A method for producing cyclohexanol by subjecting cyclohexene to a hydration reaction in the presence of water using a solid acid as a catalyst, said method using, as a reaction solvent, an organic solvent which has a solubility in water at 25° C. of not higher than 5% by weight, a boiling point which is at least 20° C. higher than that of the cyclohexanol produced, a conversion rate of not more than 3% under the hydration reaction conditions, and a solvent effect index of not less than 1.5, said solvent effect index indicating the effect of making the distribution of cyclohexene into the aqueous phase predominate.

2. A method according to claim 1, wherein the solid acid is a zeolite.

3. A method according to claim 2, wherein the zeolite is ZSM-5.

4. A method according to any one of claims 1–3, wherein the organic solvent is isophorone.

5. A method according to any one of claims 1–3, wherein the organic solvent is ethylene glycol monophenyl ether.

* * * * *